United States Patent
Rainey et al.

Patent Number: 6,106,289
Date of Patent: Aug. 22, 2000

[54] SONIC DELIVERY SYSTEM FOR DENTISTRY USING A TERFNOL DRIVER

[76] Inventors: J Tim Rainey, 403 Commerce, Refugio, Tex. 78377; Steven M. Lenos, 1747 56th St. Ct., Moline, Ill. 61265

[21] Appl. No.: 09/187,159

[22] Filed: Nov. 6, 1998

Related U.S. Application Data

[60] Provisional application No. 60/066,976, Nov. 28, 1998.

[51] Int. Cl.⁷ .............................. A61C 1/07; A61C 3/03; A61C 3/08
[52] U.S. Cl. ............................................................. 433/118
[58] Field of Search .................................... 433/118, 119, 433/121, 122, 123, 124, 125

[56] References Cited

U.S. PATENT DOCUMENTS

| | | | |
|---|---|---|---|
| 4,332,558 | 6/1982 | Lustig | 433/119 X |
| 4,417,578 | 11/1983 | Banko | 433/119 X |
| 4,496,321 | 1/1985 | Kumabe et al. | 433/119 X |
| 4,505,676 | 3/1985 | Gonser | 433/119 |
| 4,608,019 | 8/1986 | Kumabe et al. | 433/119 X |
| 5,772,434 | 6/1998 | Winston | 433/119 |

*Primary Examiner*—Nicholas D. Lucchesi
*Attorney, Agent, or Firm*—Royston, Rayzor, Vickery, Novak & Druce, L.L.P.

[57] ABSTRACT

A sonic delivery system for dentistry. The sonic delivery system includes a hand piece housing an exciting energy source connected to a driver rod which is further releasably engaged with an energy transfer tip. The driver rod linearly extends and contracts in response to the exciting energy source producing a reciprocating linear movement of the driver and energy transfer tip. In one embodiment, a rotary coupler is connected to the driver to convert the reciprocating linear movement of the driver into rotary movement of the energy transfer tip. Preferably the exciting energy source is alternating current and the driver is a rod constructed of terfnol material.

9 Claims, 1 Drawing Sheet

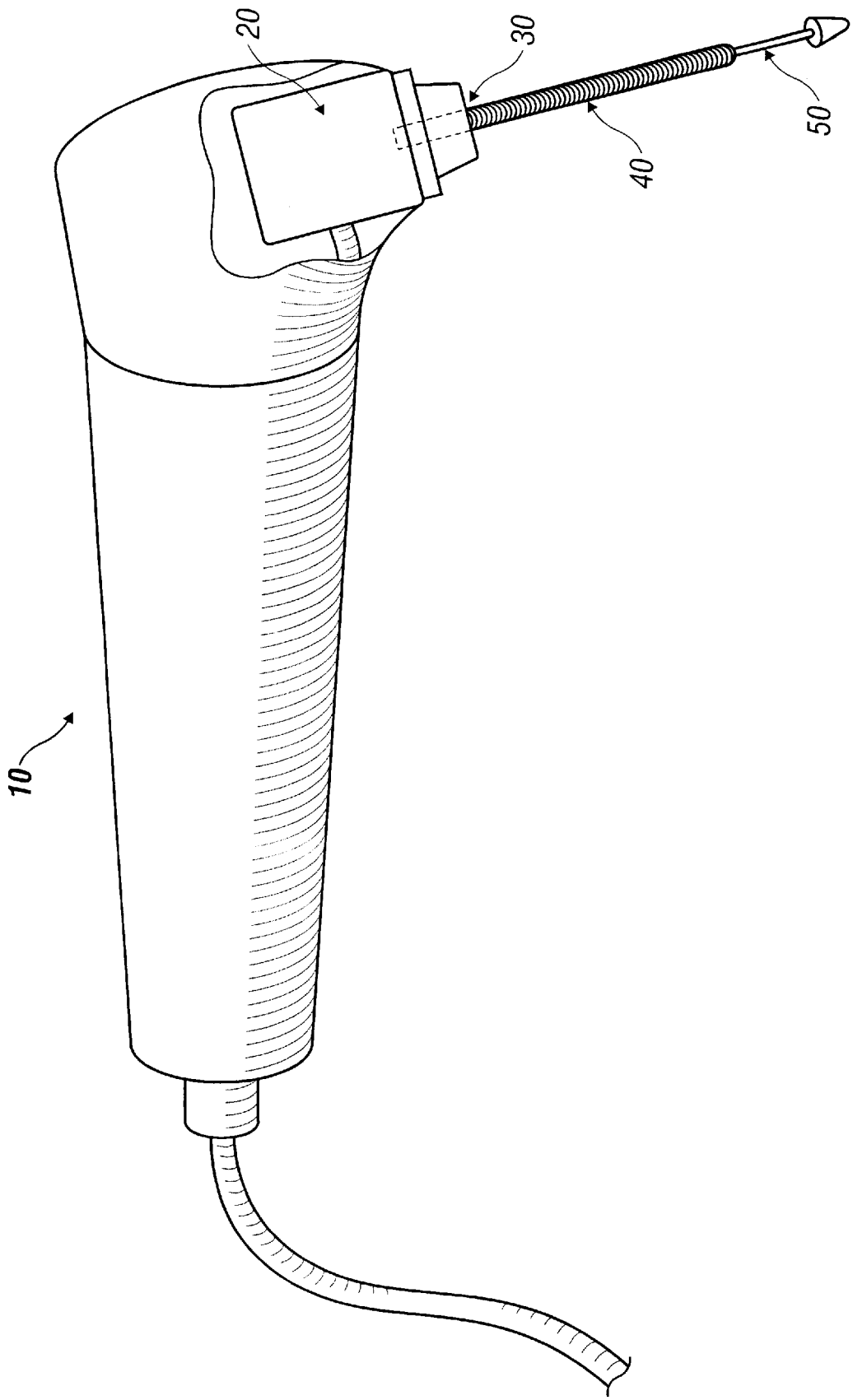

SONIC DELIVERY SYSTEM FOR DENTISTRY USING A TERFNOL DRIVER

RELATED PATENT APPLICATIONS

This patent application claims priority to U.S. Provisional Application Ser. No. 60/066,976 filed Nov. 28, 1998 entitled SONIC DELIVERY SYSTEM FOR DENTISTRY USING A TERFNOL DRIVER, said application in its entirety is hereby expressly incorporated by reference into the present application.

DESCRIPTION

1. Technical Field

The present invention relates generally to the dental field, and more specifically to sonically driven hand pieces for utilization in dental procedures.

2. Background Art

It is known within the dental industry to use sonic energy to drive apparatus used in dental procedures. The primary drawback and impediment to utilizing such sonic energy is that the motors for establishing the sonic energy or power are exceedingly high energy consumers, and their bulk makes inclusion in a suitably sized hand piece difficult, if not impossible. Therefore, those professionals and practitioners familiar with dental procedures would recognize a need for a sonic energy or power producer that is both energy efficient and sufficiently compact to be incorporated into a hand piece conducive to modern dental procedures.

In view of the above described deficiencies associated with the use of sonic energy to drive apparatus used in dental procedures, the present invention has been developed to alleviate these drawbacks and provide further benefits to the user. These enhancements and benefits are described in greater detail hereinbelow with respect to several alternative embodiments of the present invention.

DISCLOSURE OF THE INVENTION

The present invention in its several disclosed embodiments alleviates the drawbacks described above with respect to known sonic energy and power producers for dental hand pieces and incorporates several additionally beneficial features.

In the disclosed embodiment, the present invention alleviates the drawbacks described above with respect to and incorporates additional beneficial features.

The present invention utilizes a terfnol rod as a motor for generating sonic and/or ultrasonic energy and power. The energy and power are generated when the terfnol rod is excited by either direct or alternating electrical current. Responsive to such current, the terfnol rod acts as a multiplier or enhancer of the input energy which is manifested in linear extending and constricting actions. The extension and contraction establishes reciprocating motion that can be used to drive other instruments. Not only can the reciprocating linear action be directly utilized, but with appropriate accessories, the reciprocating motion may be translated into rotary motion. With these two possible forms of power output, many and various present and future dental, as well as other medical appliances may be driven using the energy and space conservative hand piece of the present invention.

The beneficial effects described above apply generally to each of the exemplary descriptions and characterizations of the devices and mechanisms disclosed herein. The specific structures through which these benefits are delivered will be described in detail hereinbelow.

BRIEF DESCRIPTION OF THE DRAWINGS

The invention will now be described in greater detail in the following way of example only and with reference to the attached drawings, in which:

FIG. 1 is a schematic cutaway illustration of a hand piece incorporating a terfnol rod driver.

MODE(S) FOR CARRYING OUT THE INVENTION

As required, detailed embodiments of the present invention are disclosed herein; however, it is to be understood that the disclosed embodiments are merely exemplary of the invention that may be embodied in various and alternative forms. The FIGURES are not necessarily to scale, some features may be exaggerated or minimized to show details of particular components. Therefore, specific structural and functional details disclosed herein are not to be interpreted as limiting, but merely as a basis for the claims and as a representative basis for teaching one skilled in the art to variously employ the present invention.

Furthermore, elements may be recited as being "coupled"; this terminology's use contemplates elements being connected together in such a way that there may be other components interstitially located between the specified elements, and that the elements so specified may be connected in fixed or movable relation one to the other.

Referring to FIG. 1, a hand piece 10 is illustrated which may be used in any of many applications wherein an efficient and compact driver is required that can supply reciprocating power directly, or rotary power upon easy conversion. The invention includes a driver 30 having a terfnol rod 40 placed in communication with an exciting energy source 20. That source of exciting energy may be either direct or alternating electrical current. In response to the current 20, the terfnol rod 40 linearly, or lengthwise, extends and constricts thereby producing reciprocating linear movement and therefore power to any energy transfer tip 50 coupled thereto. As indicated hereinabove, this reciprocating driving power may be used directly to drive a selected energy transfer tip 50, or the driving rod 40 may be coupled to a rotary converter that may then be used to supply rotary power to different types of accessories or attachments.

Although the present invention has been described and illustrated in detail, it is to be clearly understood that the same is by way of illustration and example only, and is not to be taken as a limitation. While the preferred embodiment has been described herein relative to dental applications, it should be appreciated that the invention as described herein may be utilized in any industry or field wherein compact and energy efficient hand piece drivers are desirable for providing reciprocating or rotary driving power. The spirit and scope of the present invention are to be limited only by the terms of any claims that may be presented hereafter.

INDUSTRIAL APPLICABILITY

The present invention finds applicability in all industries wherein hand held devices utilizing reciprocating and rotary motion are desired; more specifically, the present invention finds special utility in the dental field.

What is claimed and desired to be secured by Letters Patent is as follows:

1. A sonic delivery system for use in the treatment of tooth structures, said system comprising:

a handpiece configured to house an exciting energy source and shaped for hand use;

a driver coupled to said housing and engaged with said exciting energy source, said driver adapted to linearly extend and contract responsively to said exciting energy source for producing reciprocating linear movement in at least a portion of said driver and said driver being a rod comprising terfnol; and an energy transfer tip releaseably coupled to said driver, said energy transfer tip adapted for contact upon a tooth structure.

2. The system as recited in claim 1; wherein said energy source is a direct electrical current.

3. The system as recited in claim 1; wherein said energy source is an alternating electrical current.

4. A sonic delivery system for use in the treatment of tooth structures, said system comprising:

a handpiece configured to house an exciting energy source and shaped for hand use;

a driver coupled to said housing and engaged with said exciting energy source, said driver adapted to linearly extend and contract responsively to said exciting energy source for producing reciprocating linear movement in at least a portion of said driver and said driver is a rod substantially comprised of terfnol; and an energy transfer tip releaseably coupled to said driver, said energy transfer tip adapted for contact upon a tooth structure.

5. The system as recited in claim 1; wherein a rotary coupler is connected at a first end to said driver and a second end is releaseably engaged to said energy transfer tip, said rotary coupler adapted to convert reciprocating linear movement of said driver to rotary movement of said energy tip.

6. The system as recited in claim 1; wherein said rotary coupler is releaseably engaged to said driver.

7. A sonic delivery system for use in the treatment of tooth structures, said system comprising:

an exciting energy source; and a driver engaged with said exciting energy source, said driver adapted to linearly extend and contract responsively to said exciting energy source for producing reciprocating linear movement in at least a portion of said driver, said driver being a member comprising terfnol.

8. The sonic delivery system as recited in claim 7, further comprising:

an energy transfer device releaseably coupled to said driver, said energy transfer device adapted for contact upon a tooth structure.

9. A sonic delivery system for use in the treatment of tooth structures, said system comprising:

an exciting energy source;

a driver engaged with said exciting energy source, said driver adapted to extend and contract responsively to said exciting energy source for producing driving movement in at least a portion of said driver, said driver being a member comprising terfnol; and an energy transfer device releaseably coupled to said driver, said energy transfer device adapted for contact upon a tooth structure.

* * * * *